United States Patent [19]
Thornton et al.

[11] Patent Number: 5,616,114
[45] Date of Patent: Apr. 1, 1997

[54] INTRAVASCULAR RADIOTHERAPY EMPLOYING A LIQUID-SUSPENDED SOURCE

[75] Inventors: Richard T. Thornton, League City; Anthony J. Bradshaw, Missouri City; Wayne W. Snyder, Houston, all of Tex.

[73] Assignee: Neocardia, LLC., Houston, Tex.

[21] Appl. No.: 352,318

[22] Filed: Dec. 8, 1994

[51] Int. Cl.$^6$ .................................................. A61N 5/00
[52] U.S. Cl. .................................................. 600/3
[58] Field of Search ........................ 600/1–8; 606/7, 606/108, 192, 194, 198

[56] References Cited

U.S. PATENT DOCUMENTS

| | | | |
|---|---|---|---|
| 3,324,847 | 6/1967 | Zoumboulis | 128/1.2 |
| 4,364,376 | 12/1982 | Bigham | 600/5 |
| 4,601,713 | 7/1986 | Fuqua | 604/280 |
| 5,199,939 | 4/1993 | Dake et al. | 600/3 |
| 5,213,561 | 5/1993 | Weinstein et al. | 600/3 |
| 5,334,154 | 8/1994 | Samson et al. | 604/102 |

FOREIGN PATENT DOCUMENTS 9304735  3/1993  WIPO ........................ 600/7

*Primary Examiner*—Angela D. Sykes
*Assistant Examiner*—John P. Lacyk
*Attorney, Agent, or Firm*—Wigman, Cohen, Leitner & Myers, P.C.

[57] ABSTRACT

Apparatus and methods are provided for delivering an easily controllable inherently uniform dosage of radiation to the walls of a blood vessel for preventing restenosis after angioplasty. The apparatus comprises a catheter having a balloon tip which is inflatable with a liquid containing a suspended radioactive material such as $^{125}$I or $^{32}$P. The catheter is advanced through the patient until this treatment balloon is disposed in the stenosed region of the blood vessel. The balloon is filled with the radioactive fluid which simultaneously expands and relieves the stenosis while irradiating the tissue, or if the stenosis has previously been relieved, the target tissue is irradiated by filling the treatment balloon with the radioactive fluid until the outer wall of the balloon engages, without substantially expanding, the inner wall of the blood vessel. An outer containment balloon is also provided to prevent loss of radioactive fluid in the event the treatment balloon ruptures and which may be used to perform the angioplasty prior to filling the treatment balloon with the radioactive fluid. The treatment balloon may be configured to minimize the volume of radioactive fluid necessary by providing an inner balloon filled with an inert material or by configuring the treatment balloon itself as a hollow cylinder with an annular chamber for receiving the radioactive fluid.

24 Claims, 6 Drawing Sheets

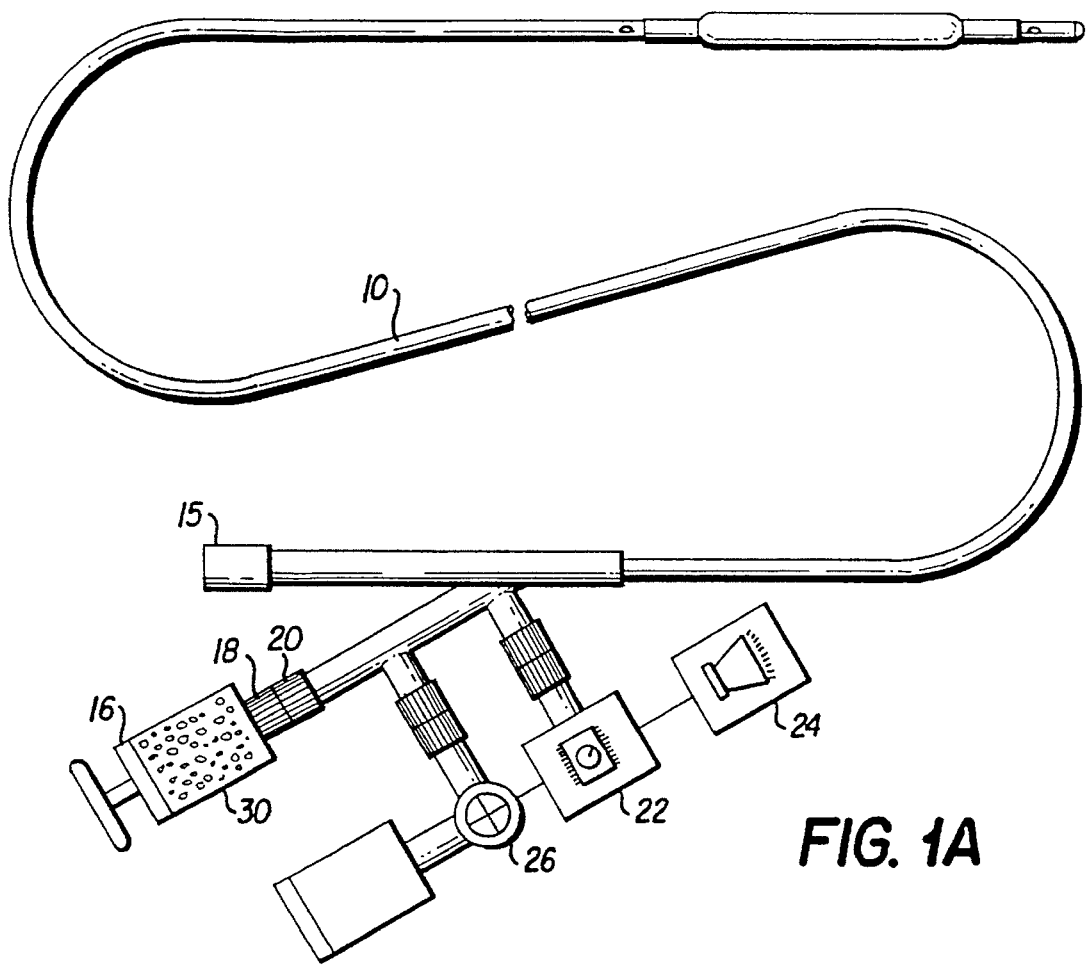
FIG. 1A
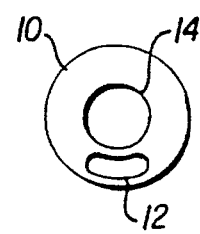
FIG. 1B
FIG. 1C
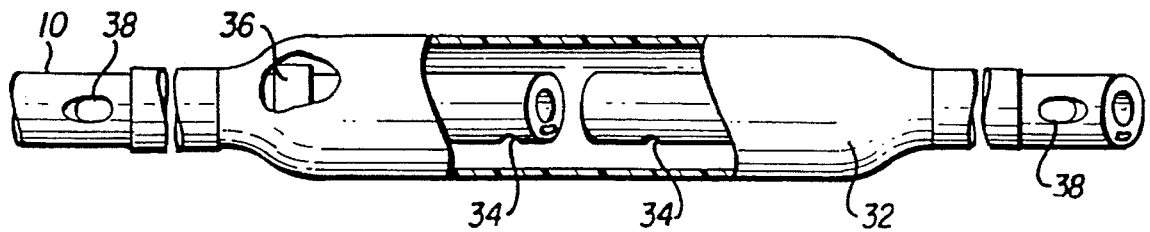

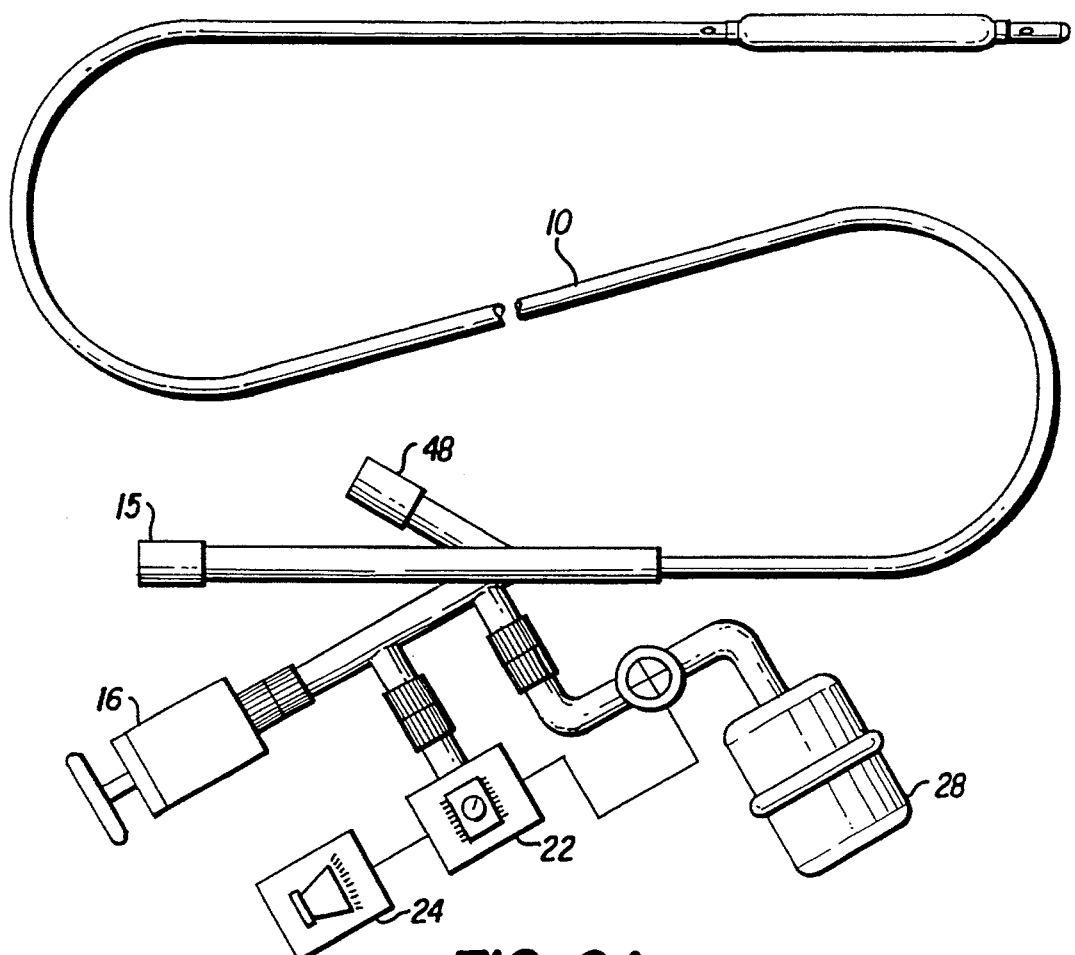
FIG. 2A
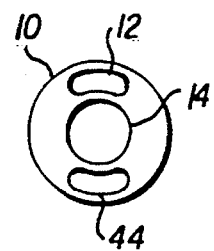
FIG. 2B
FIG. 2C
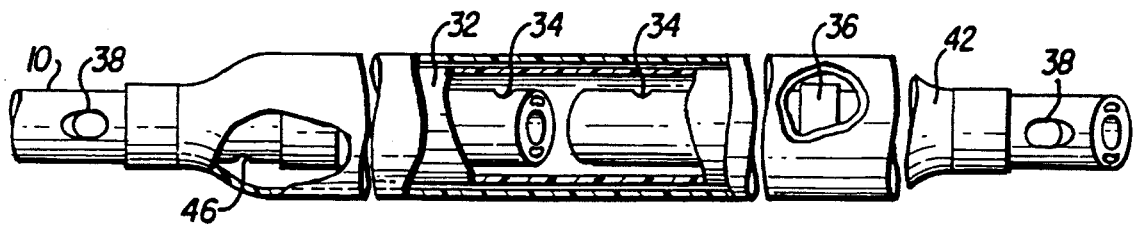

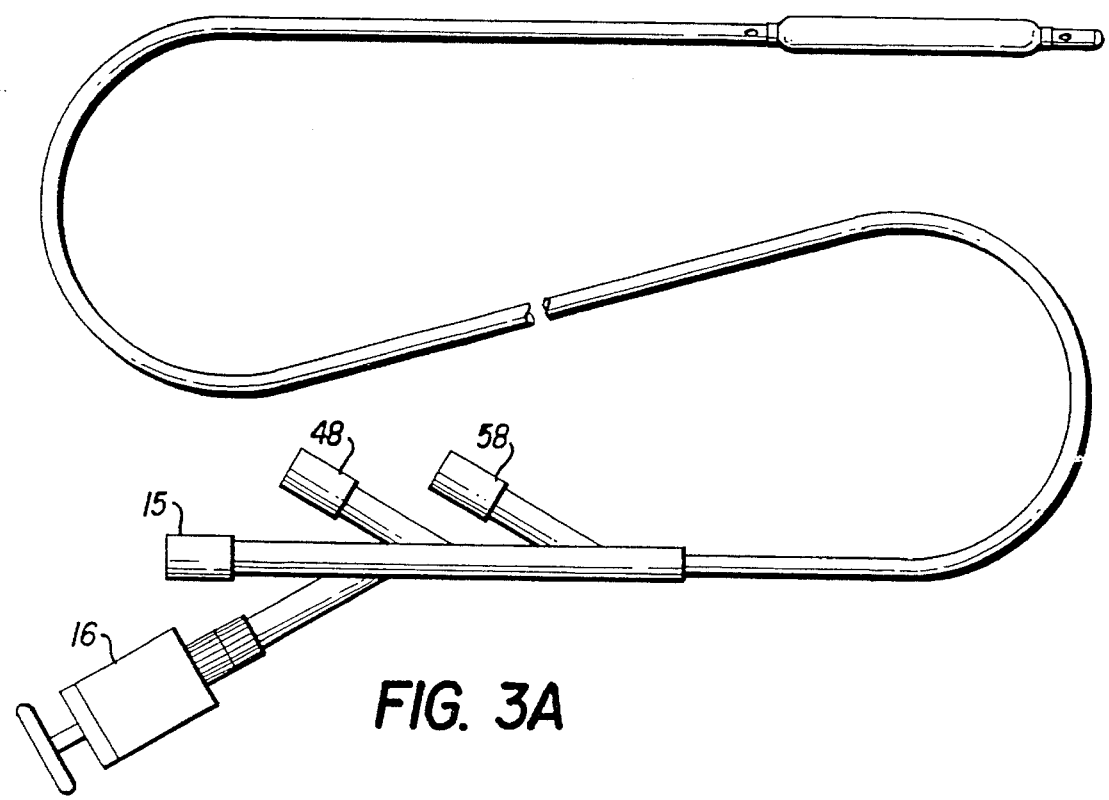
FIG. 3A
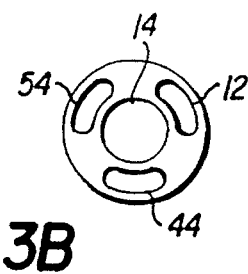
FIG. 3B
FIG. 3C
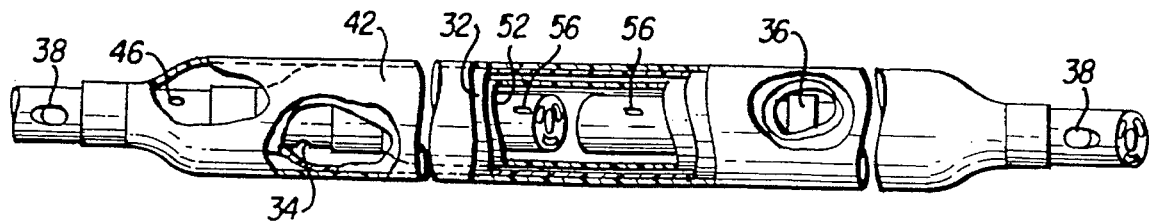

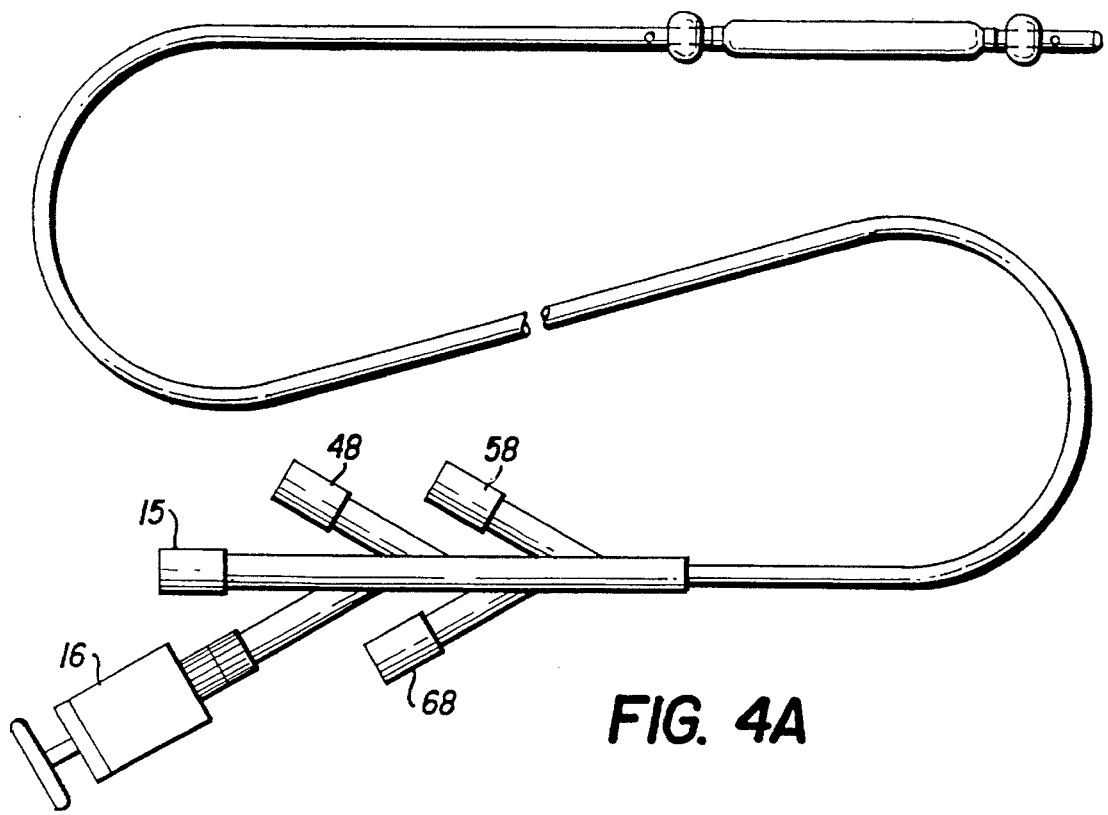
FIG. 4A
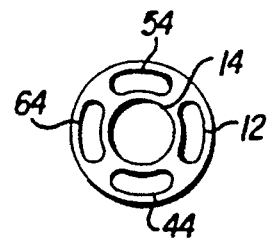
FIG. 4B
FIG. 4C
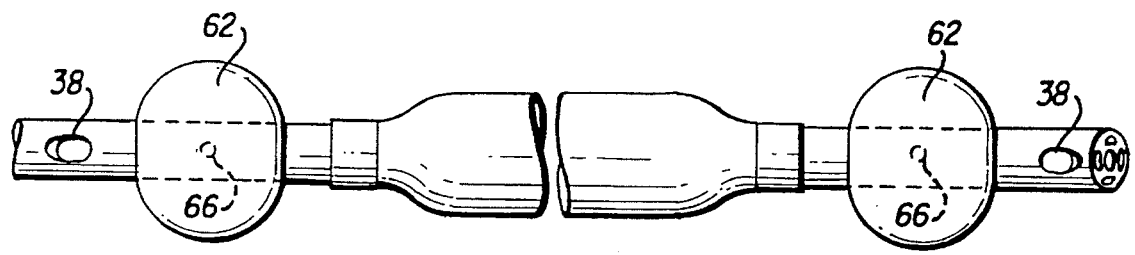

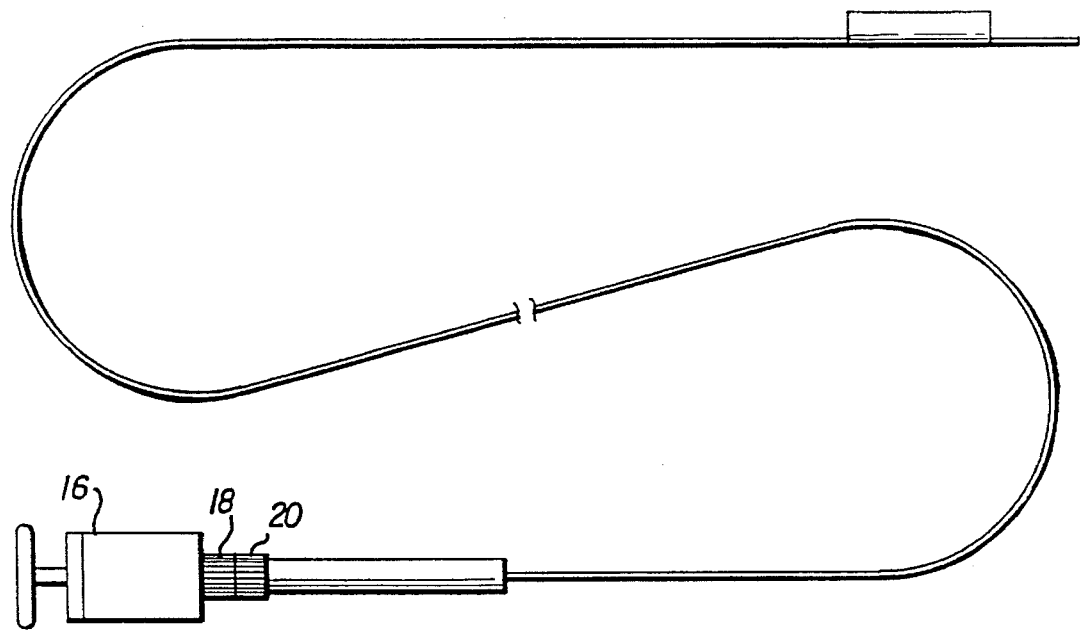
FIG. 6A
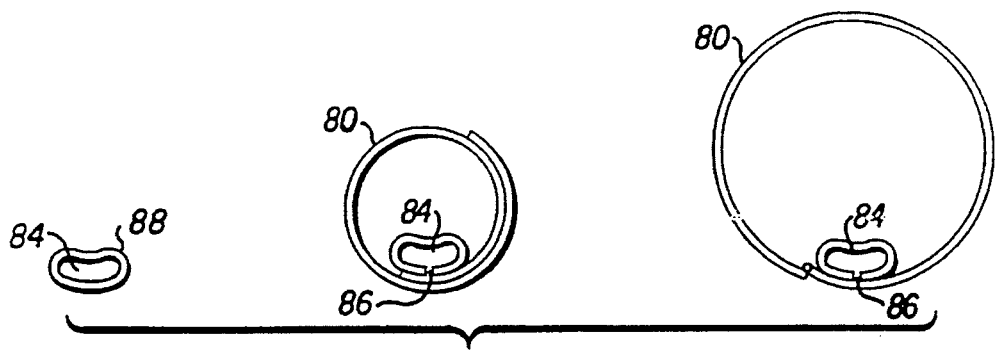
FIG. 6B
FIG. 6C
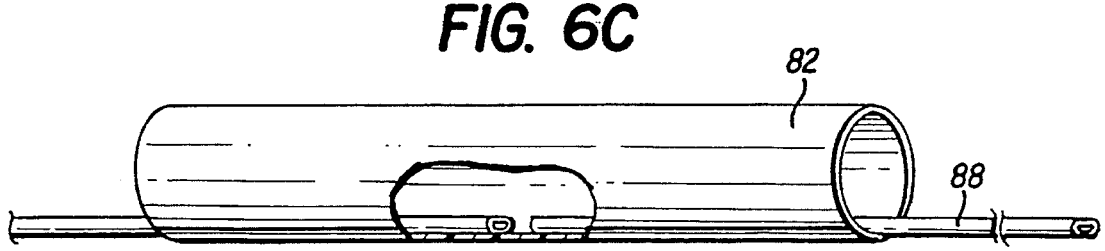

INTRAVASCULAR RADIOTHERAPY EMPLOYING A LIQUID-SUSPENDED SOURCE

BACKGROUND OF THE INVENTION

This invention relates generally to treatment of selected tissue by inter-vivo radiation, specifically to radiation treatment of selected regions of the cardiovascular system that have been subjected to trauma to prevent restenosis of the traumatized region, more specifically to radiation treatment to prevent restenosis of an artery traumatized by percutaneous transluminal angioplasty (PTA).

PTA treatment of the coronary arteries, percutaneous transluminal coronary angioplasty (PTCA), also known as balloon angioplasty, is the predominant treatment for coronary vessel stenosis. Approximately 300,000 procedures were performed in the United States (U.S.) in 1990 and an estimated 400,000 in 1992. The U.S. market constitutes roughly half of the total market for this procedure. The increasing popularity of the PTCA procedure is attributable to its relatively high success rate, and its minimal invasiveness compared with coronary by-pass surgery. Patients treated by PTCA, however, suffer from a high incidence of restenosis, with about 35% of all patients requiring repeat PTCA procedures or by-pass surgery, with attendant high cost and added patient risk. More recent attempts to prevent restenosis by use of drugs, mechanical devices, and other experimental procedures have had limited success.

Restenosis occurs as a result of injury to the arterial wall during the lumen opening angioplasty procedure. In some patients, the injury initiates a repair response that is characterized by hyperplastic growth of the vascular smooth muscle cells in the region traumatized by the angioplasty. The hyperplasia of smooth muscle cells narrows the lumen that was opened by the angioplasty, thereby necessitating a repeat PTCA or other procedure to alleviate the restenosis.

Preliminary studies indicate that intravascular radiotherapy (IRT) has promise in the prevention or long-term control of restenosis following angioplasty. It is also speculated that IRT may be used to prevent stenosis following cardiovascular graft procedures or other trauma to the vessel wall. Proper control of the radiation dosage, however, is critical to impair or arrest hyperplasia without causing excessive damage to healthy tissue. Overdosing of a section of blood vessel can cause arterial necrosis, inflammation and hemorrhaging. Underdosing will result in no inhibition of smooth muscle cell hyperplasia, or even exacerbation of the hyperplasia and resulting restenosis.

U.S. Pat. No. 5,059,166 to Fischell discloses an IRT method that relies on a radioactive stent that is permanently implanted in the blood vessel after completion of the lumen opening procedure. Close control of the radiation dose delivered to the patient by means of a permanently implanted stent is difficult to maintain because the dose is entirely determined by the activity of the stent at the particular time it is implanted. Additionally, the dose delivered to the blood vessel is non-uniform because the tissue that is in contact with the individual strands of the stent receive a higher dosage than the tissue between the individual strands. This non-uniform dose distribution is especially critical if the stent incorporates a low penetration source such as a beta emitter.

U.S. Pat. No. 5,302,168 to Hess teaches use of a radioactive source contained in a flexible carrier with remotely manipulated windows. H. Böttcher, et al. of the Johann Wolfgang Goerhe University Medical Center, Frankfurt, Germany report in November 1992 of having treated human superficial femoral arteries with a similar endoluminal radiation source. These methods generally require use of a higher activity source than the radioactive stent to deliver an effective dose. Accordingly, measures must be taken to ensure that the source is maintained reasonably near the center of the lumen to prevent localized overexposure of tissue to the radiation source. Use of these higher activity sources also dictates use of expensive shielding and other equipment for safe handling of the source.

What is needed theta, is an IRT method and apparatus that delivers an easily controllable uniform dosage of radiation to the walls of the blood vessel without the need for special measures to center a radiation source in the lumen, the need for expensive shielding to protect medical personnel, or the need for expensive remote afterloaders to handle the higher activity sources.

SUMMARY OF THE INVENTION

According to the present invention the IRT procedure is accomplished either during or after the angioplasty procedure, by advancing a flexible catheter having a balloon at the distal tip through the cardiovascular system of the patient until this treatment balloon is positioned at a target area comprising the stenosed or recently re-opened region of the blood vessel. In the case of simultaneous-angioplasty IRT the treatment balloon is filled with a fluid containing a radioactive material which simultaneously expands and relieves the stenosis while irradiating the tissue in the target area of the blood vessel. In the case of post-angioplasty IRT, the stenosis is first relieved, then the target tissue is irradiated by filling the treatment balloon with the radioactive fluid until the outer wall of the balloon engages, without substantially expanding, the inner wall of the blood vessel.

In one embodiment of the present invention, the radioactive material is a suspension of a beta emitting material such as $^{125}$I or $^{32}$P. The substantially pure beta radiation emitted by such sources is quickly absorbed by surrounding tissue and will not penetrate substantially beyond the walls of the blood vessel being treated. Accordingly, incidental irradiation of the heart and other organs adjacent to the treatment site is substantially eliminated. Moreover, because the radioactive fluid has a substantially uniform suspension of radioactive material, the radiation emitted at the surface of the balloon in contact with the target area of the blood vessel is inherently uniform. Accordingly, uniform irradiation of the blood vessel wall is also inherent. The catheter of the present invention may be equipped with perfusion ports proximal and distal of the balloon to permit blood flow past the balloon when inflated.

According to another embodiment of the present invention, a second balloon is provided that completely envelopes the treatment balloon. This containment balloon acts as a containment vessel in the event the inner treatment balloon ruptures when filled with the radioactive fluid. In use, prior to filling the treatment balloon with the radioactive fluid, the containment balloon is filled, preferably with a non-toxic radio-opaque liquid, to verify the integrity of the containment balloon. The radio-opaque fluid filled containment balloon may also be used to verify correct positioning of the catheter within the target area of the blood vessel.

According to another embodiment of the present invention, an inner inert expansion balloon is provided inside the treatment balloon. The inert expansion balloon reduces the amount of radioactive fluid that must be used to fill the treatment balloon by occupying space within the middle balloon that would otherwise be filled with radioactive fluid. In use, prior to filling the treatment balloon with the radioactive fluid, the inert expansion balloon is filled with an inert liquid, thereby forcing the radioactive fluid to the periphery of the treatment balloon. Because of the self-attenuation of the radioactive fluid itself, most of the radioactivity originates at the surface of the treatment balloon. Accordingly, the surface radiation is not reduced substantially as a result of the center being filled with an inert material. Accordingly, the same radiation level can be achieved as if the treatment balloon were completely filled with radioactive fluid, while using substantially less radioactive fluid. A further refinement of this embodiment, especially suited to larger lumens, incorporates a substantially hollow cylindrical balloon having a relatively small cavity between the inner and outer wall of the cylinder into which the radioactive fluid is injected.

According to another embodiment of the present invention, a proximal and distal blocking balloon are also provided to contain the radioactive fluid in the target area in the event of a total failure of all containment systems.

BRIEF DESCRIPTION OF THE DRAWINGS

The above and other objects, aspects, features and attendant advantages of the present invention will become apparent from a consideration of the ensuing detailed description of presently preferred embodiments and methods thereof, taken in conjunction with the accompanying drawings, in which:

FIG. 1A, 1B, 1C are plan and cross sectional views of an apparatus according to the present invention;

FIG. 2A, 2B, 2C are plan and cross sectional views of an alternate embodiment of an apparatus according to the present invention incorporating a containment balloon;

FIG. 3A, 3B, 3C are plan and cross sectional views of an alternate embodiment of an apparatus according to the present invention incorporating an inner inert expansion balloon;

FIG. 4A, 4B, 4C are plan and cross sectional views of an alternate embodiment of an apparatus according to the present invention incorporating proximal and distal blocking balloons;

FIG. 6A, 6B, 6C are plan and cross sectional views of an alternate embodiment of an apparatus according to the present invention incorporating a sleeve suitable for positioning with an angioplasty balloon.

DESCRIPTION OF PREFERRED EMBODIMENTS AND METHODS

Figure 5A:
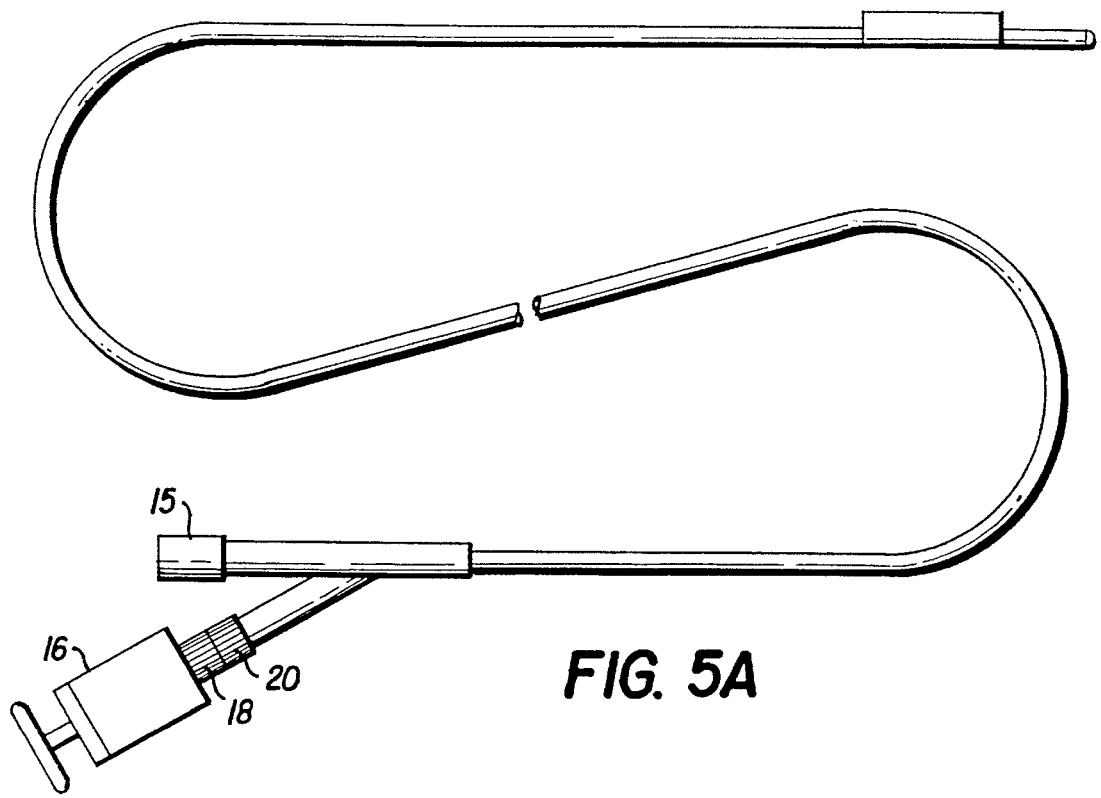
FIG. 5A, 5B, 5C are plan and cross sectional views of an alternate embodiment of an apparatus according to the present invention incorporating an inflatable sleeve.

FIGS. 1A and 1B illustrate a suspended-isotope IRT catheter according to the present invention. The IRT catheter comprises shaft 10 having a longitudinal inflation lumen 12, a conventionally formed tip, and may include longitudinal guidewire/injection/perfusion lumen 14. Shielded injector 16, which may be a manual or automated syringe containing a radioactive liquid 30, or a pump connected to a reservoir of radioactive liquid 30, is connected to the proximal end of shaft 10 and is in fluid communication with inflation lumen 12. To prevent possible spillage and corresponding radioactive contamination of the operating room and/or its personnel, the shielded injector 16 is permanently attached to shaft 10, or preferably, injector 16 is equipped with a fail-safe non-detachable connector 18, which cannot be detached from the corresponding receptacle 20 of shaft 10 once it is attached thereto. Non-detachable connector 18 also prevents the radioactive fluid 30 from being discharged from injector 16 until the connector is connected to the receptacle in shaft 10. Connectors having ring-detents and other non-detachable fluid fittings are well known in the art, as are piercing valves and other common methods of preventing fluid flow prior to attachment of a fluid fitting. The proximal end of shaft 10 also includes guidewire lumen luer fitting 15 in fluid communication with guidewire lumen 14, through which drugs may be injected directly into the patient's blood stream.

FIG. 1C is an enlarged view of the distal end of the present embodiment of the catheter. Treatment balloon 32 comprises an elastic or preferably an inelastic balloon, which may preferably be made from polyethylene terephthalate (PET), polyvinyl chloride (PVC), or other medical grade material suitable for constructing a strong non-compliant balloon. Treatment balloon 32 is sealed at its proximal and distal ends to catheter shaft 10 in fluid communication with inflation lumen 12 via inflation lumen ports 34. Immediately inside proximal and distal ends of balloon 32 are markers 36 (only are shown), comprising bands of silver or other suitable x-ray opaque material. Markers 36 aid in the proper positioning of balloon 32 within the target area of the blood vessel under fluoroscopy. Immediately adjacent to and outside the ends of balloon 32 are perfusion ports 38, which are in fluid communication with guidewire lumen 14. Perfusion ports are well known in the art as a means of permitting some blood flow past a balloon that is inflated within and otherwise blocking a blood vessel.

In operation, after the angioplasty or other unblocking procedure has been performed, a suspended-isotope IRT catheter having a treatment balloon of the appropriate size is selected. The catheter is positioned within the patient's blood vessel by conventional means so that the balloon is within the target area. The shielded injector 16 is connected to the receptacle at the proximal end of the catheter shaft and the air is evacuated from the balloon and inflation lumen, in the case of a shielded syringe, by withdrawing the plunger. The balloon is then filled with the liquid containing the suspended isotope until the outer wall of the balloon engages the inner wall of the blood vessel. The balloon is maintained in this inflated state for a predetermined period of time calculated to deliver an effective dose of radiation to the wall of the blood vessel. The fluid is then withdrawn from the balloon and the catheter withdrawn from the patient's body. To reduce the chances of overpressurizing the treatment balloon and causing a rupture, pressure feedback device 22 is connected to the proximal end of inflation lumen 12. Pressure feedback device 22 may be a pressure gauge, or preferably a solid-state pressure transducer that operates an alarm 24 and/or a waste gate 26 in the event an overpressure condition is detected. Alternately, the solid state pressure transducer may be positioned at the distal end of the inflation lumen to monitor pressure in the balloon directly. It may also be possible to combine the angioplasty steps with the radiation treatment by using a catheter according to the present invention to perform the unblocking procedure.

FIGS. 2A–2C illustrate an alternate embodiment of the present invention further including an outer containment balloon 42. Containment balloon 42 is an inelastic or preferably an elastic balloon, which is preferably made of latex or other medical grade material suitable for constructing puncture-resistant elastic balloons. Containment balloon 42 is attached at its proximal and distal ends to shaft 10 and completely surrounds treatment balloon 32. Containment balloon 42 is in communication with containment balloon inflation lumen 44 via containment balloon inflation lumen port 46, which in turn is in fluid communication with containment balloon luer fitting 48 at the proximal end of shaft 10.

In operation, after the IRT catheter is in position but before treatment balloon 32 is filled with the radioactive liquid, containment balloon 42 is filled with a commonly used non-toxic radio-opaque contrast medium injected through containment balloon luer fitting 48. The integrity of containment balloon is verified by fluoroscopy, pressure, or other suitable means and, if integrity is confirmed, the radio-opaque liquid is withdrawn and the procedure for injecting the radioactive fluid into treatment balloon 32 carried out. If the integrity of the containment balloon has been compromised (for example by sharp edges in guide catheters, guide wires, stents, etc.) a new catheter is selected and repositioned. By verifying integrity of the containment balloon after the balloon is in position, but before the radioactive fluid is injected, a substantial degree of safety against accidental injection of radioactive fluid into the patient's blood stream is achieved. Where a containment balloon is used (or blocking balloons as discussed with reference to FIGS. 4A–4C are used), pressure feedback device 22 may also be used to activate an emergency evacuation system. In the event the pressure feedback device detected a sudden drop in pressure (indicating rupture of the treatment balloon) the pressure feedback device would initiate an immediate withdrawal of all radioactive fluid from the patient, for example by opening a valve to a vacuum accumulator 28. It may also be practicable to perform the angioplasty and the radiation treatment with a single catheter by using the containment balloon of the invention to perform the unblocking procedure prior to filling the treatment balloon with the radioactive fluid. In such a case, the containment balloon would preferably be inelastic and the treatment balloon elastic.

Several important considerations must be balanced in the design of an apparatus for safely and effectively injecting a radioactive fluid into a patient to irradiate a blood vessel to prevent restenosis. Although both $^{125}I$ and $^{32}P$ are substantially pure beta radiation emitters, $^{32}P$ is the preferred isotope for suspended-isotope IRT because it has a half-life of only 14.3 days as compared with the 60 day half-life of $^{125}I$. A shorter half life renders $^{32}P$ safer to use because, in the event of a catastrophic failure involving leakage of radioactive fluid into the patient's blood stream, for a given calculated dose rate, a shorter half life will result in a lesser total body dosage. Additionally, $^{32}P$ has been used in the treatment of chronic leukemia, where it is injected directly into a patient's blood stream. Accordingly, substantial medical knowledge exists as to the effects of $^{32}P$ in the blood stream.

In the leukemia treatment, depending on the patient's weight, a suspended radiation source of about 6 to 15 millicuries of $^{32}P$ is used. Accordingly, for maximum safety, the preferred suspended-isotope IRT catheter should also use a source of no more than 6 millicuries. Prior experiments have shown that a dose of about 1000 to 3500 rads delivered to the blood vessel wall from a gamma radiation source is effective to inhibit the smooth muscle cell hyperplasia that causes restenosis. For low penetration sources, such as beta radiation emitters, it is believed a dosage up to 5,000 rads may be tolerated. For a 6 millicurie $^{32}P$ source to deliver such a dose to the surface of the blood vessel, the balloon must be in position for substantially in excess of one minute, thus necessitating the perfusion ports.

For example, it is estimated that the balloon will absorb approximately 15% of the radiation delivered by the radioactive liquid. Accordingly, to deliver 2000 rads to the blood vessel wall, 2350 rads must be delivered to the inner wall of the balloon. A typical treatment balloon comprises a cylindrical balloon having an internal diameter of 3 millimeters, a length of about 30 millimeters, and an interior volume of approximately 0.2 cubic centimeters. Accordingly, to limit the total source to no more than 6 millicuries, 0.2 cubic centimeters of a liquid having a source concentration of no more than 30 millicuries per cubic centimeter must be used. A 30 millicurie per cubic centimeter source, however, requires about 6 minutes to deliver 2350 rads to the interior of the 3 millimeter diameter treatment balloon and thus requires about 6 minutes to deliver 2000 rads to the interior wall of the blood vessel.

The larger the balloon, the lower the concentration of the radiation source in the liquid must be to maintain the safe limit of 6 millicuries. However, the lower the concentration, the lower the dose rate and the longer the balloon must remain inflated to deliver an effective dose to the blood vessel wall.

FIGS. 3A–3C illustrate an embodiment of the present invention incorporating an inner inert expansion balloon 52. Inert expansion balloon 52 is an elastic or preferably an inelastic balloon, which may preferably be made from PET, PVC, or other medical grade material suitable for constructing a strong non-compliant balloon. Expansion balloon 52 is sealed at its proximal and distal ends to catheter shall 10 completely within treatment balloon 32 and is in fluid communication with inert expansion balloon lumen 54 via expansion lumen ports 56. Inert expansion balloon lumen 54 is, in turn, in fluid communication with inert expansion balloon luer fitting 58 at the proximal end of shaft 10.

In operation, before treatment balloon 32 is filled with radioactive fluid, inert expansion balloon 52 is filled with an inert liquid injected through expansion balloon luer fitting 58. Because the fluid near the center of a body of radioactive fluid does not contribute significantly to the radiation emitted from the surface of the body, by filling the center of the balloon with an inert filler, a smaller volume of radioactive liquid can be used without significantly affecting the radiation delivered to the vessel wall. Without the inert filler, to avoid exceeding the 6 millicurie limit, the same size treatment balloon would require a larger volume of lower concentration radioactive fluid, with a commensurately lower dose rate and longer required treatment interval.

FIGS. 4A–4C illustrate an additional embodiment of the present invention incorporating blocking balloons 62. Blocking balloons 62 are inelastic or preferably elastic balloons, which are preferably made of latex or other medical grade material suitable for constructing puncture-resistant elastic balloons. Blocking balloons 62 are sealed to shaft 10 proximal and distal of treatment balloon 32 between perfusion ports 38, and are in fluid communication with a common blocking balloon inflation lumen 64 via blocking balloon inflation ports 66. Blocking balloon inflation lumen 64 is, in turn, in fluid communication with blocking balloon luer fitting 68 at the proximal end of shaft 10.

In operation, blocking balloons 62 are inflated in the blood vessel until the blood flow past the balloons is substantially stopped (the flow of blood in the vessel itself continues through the perfusion ports). The treatment balloon 32 is then inflated with the radioactive fluid for treatment of the blood vessel walls. In the event treatment balloon 32 ruptures and containment balloon 42 fails, the radioactive fluid is still contained in the blood vessel between blocking balloons 62. The fluid can then be withdrawn either through any of the inflation lumens that, because of the breach, are in fluid communication with the interior of the blood vessel between the blocking balloons 62, or preferably withdrawn automatically using the emergency evacuation system discussed with reference to FIGS. 2A–2C. Blocking balloons may also be used in lieu of containment balloon 42, especially in particularly small lumens where a small profile is desirable.

Figure 5B:
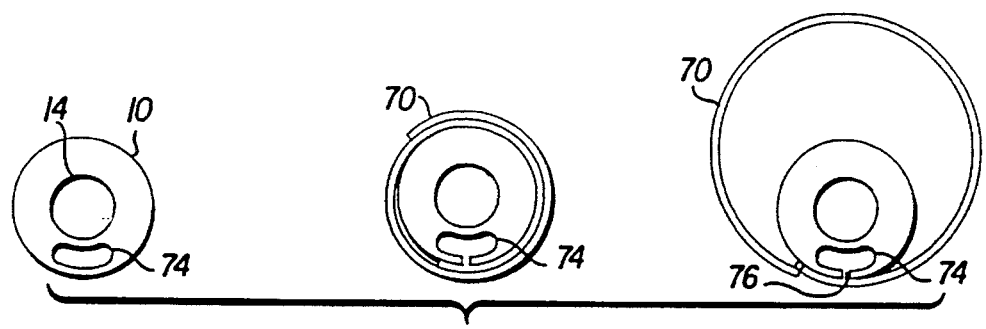
Figure 5C:
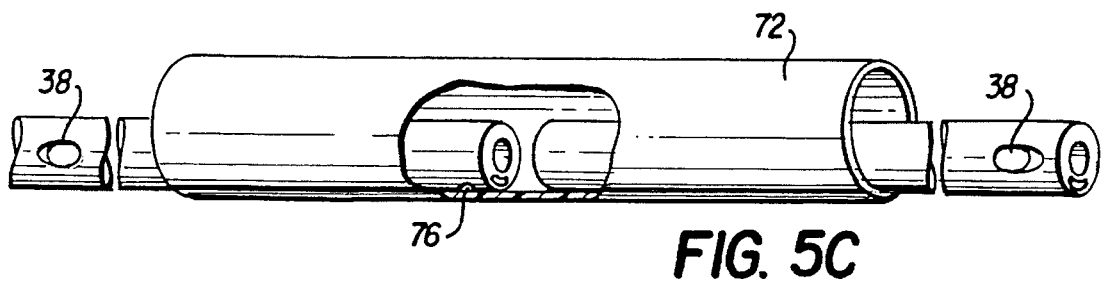

FIGS. 5A–5C illustrate an additional embodiment of the present invention incorporating a sleeve-shaped treatment balloon 72. The sleeve-shaped balloon 72 comprises a hollow cylindrical balloon having an inner wall and an outer wall defining an interior cavity 70 therebetween. Sleeve-shaped balloon is preferably inelastic, and may be preferably made from PET, PVC, or other medical grade material suitable for constructing a strong non-compliant balloon. Sleeve-shaped balloon 72 is sealed to catheter shaft 10 along a longitudinal line of contact between its interior surface and catheter shaft 10. The interior cavity 70 is in fluid communication with inflation lumen 74 via inflation lumen ports 76 at points along the length of the area of contact between shall 10 and sleeve shaped balloon 72. As with the inflation lumen 12 discussed in connection with other embodiments discussed herein, inflation lumen 74 is in fluid communication with fail-safe non-detachable receptacle 20 for receiving radioactive liquid 30.

FIGS. 6A–6C illustrate an additional embodiment of the present invention incorporating a sleeve-shaped balloon 82, comprising an inner and outer wall defining an interior chamber 80, similar to the embodiment of FIGS. 6A–6C. The sleeve-shaped balloon of the present embodiment is suitable for positioning by means of a separate catheter, such as an angioplasty balloon catheter. Accordingly, shaft 10 with guidewire lumen 14 is eliminated in favor of a low profile shaft 88 having inflation lumen 84 in fluid communication with interior chamber 80 via inflation ports 86 located along the longitudinal area of contact between shaft 88 and balloon 82.

Thus, the present invention provides a safe and effective IRT method and apparatus, which delivers an easily controllable inherently uniform dosage of radiation to the walls of a blood vessel, without the need for special measures to center a radiation source in the lumen, the need for expensive shielding to protect medical personnel, or the need for expensive remote afterloaders to handle the higher activity sources.

Although certain preferred embodiments and methods have been disclosed herein, it will be apparent from the foregoing disclosure to those skilled in the art that variations and modifications of such embodiments and methods may be made without departing from the true spirit and scope of the invention. Accordingly, it is intended that the invention shall be limited only to the extent required by the appended claims and the rules and principles of applicable law.

What is claimed is:

1. An apparatus for localized intravascular radiotherapy of a blood vessel, such as a coronary artery, comprising:

a catheter, said catheter comprising an elongate member having a proximal and a distal end, said elongate member being sized and of sufficient flexibility for introduction into a patient's body through a cardiovascular lumen until the distal end is disposed at a target area within the blood vessel, said target area comprising a wall of the blood vessel, said elongate member further including a longitudinal hole therethrough defining a fluid passage;

fluid expansible means connected to said elongate member in fluid communication with said passage for containing a fluid having a radioactive material therein; and means for introducing said fluid into said fluid passage to expand the fluid expansible means toward said wall, the radioactive material in said fluid being substantially uniformly dispersed in said fluid expansible means such that the wall of the blood vessel is substantially uniformly exposed to radiation from said radioactive material for a given treatment time.

2. The apparatus of claim 1 wherein said fluid containing a radioactive material comprises a fluid containing a material chosen from the group consisting of iodine and phosphorous.

3. The apparatus of claim 1 wherein said introducing means comprises a shielded syringe.

4. The apparatus of claim 3 wherein said shielded syringe is permanently attached to said catheter.

5. The apparatus of claim 4 wherein said shielded syringe further includes a fail-safe non-detachable fluid coupling and said catheter includes a corresponding fail-safe non-detachable receptacle.

6. The apparatus of claim 1 wherein said introducing means comprises a pump.

7. The apparatus of claim 6 wherein said pump is permanently attached to said catheter.

8. The apparatus of claim 7 wherein said pump further includes a fail-safe non-detachable fluid coupling and said catheter includes a corresponding fail-safe non-detachable receptacle.

9. An apparatus for localized intravascular radiotherapy of a blood vessel, such as a coronary artery, comprising:

a catheter, said catheter comprising an elongate member having a proximal and a distal end, said elongate member being sized and of sufficient flexibility for introduction into a patient's body through a cardiovascular lumen until the distal end is disposed at a target area within the blood vessel, said elongate member further including a longitudinal hole therethrough defining a treatment balloon inflation lumen;

a treatment balloon, said treatment balloon comprising an inflatable balloon having an interior chamber, said treatment balloon being sealed to the distal end of said elongate member with the interior chamber of said treatment balloon in fluid communication with said treatment balloon inflation lumen;

means for introducing a fluid containing a radioactive material into said treatment balloon inflation lumen to fill the interior chamber of said treatment balloon for exposure of said target area to said radioactive material for a predetermined period of time; and means for detecting pressure in said treatment balloon inflation lumen.

10. An apparatus for localized intravascular radiotherapy of a blood vessel, such as a coronary artery, comprising:

a catheter, said catheter comprising an elongate member having a proximal and a distal end, said elongate member being sized and of sufficient flexibility for introduction into a patient's body through a cardiovascular lumen until the distal end is disposed at a target area within the blood vessel, said elongate member further including a longitudinal hole therethrough defining a treatment balloon inflation lumen;

a treatment balloon, said treatment balloon comprising a first inflatable balloon having an interior chamber, said treatment balloon being sealed to the distal end of said elongate member with the interior chamber of said treatment balloon in fluid communication with said treatment balloon inflation lumen;

means for introducing a fluid containing a radioactive material into said treatment balloon inflation lumen to fill the interior chamber of said treatment balloon for exposure of said target area to said radioactive material for a predetermined period of time; and a containment balloon, said containment balloon comprising a second inflatable balloon having an interior chamber, said containment balloon being sealed to the distal end of said elongate member with said interior chamber of said containment balloon surrounding said treatment balloon.

11. The apparatus of claim 10 wherein said elongate member further includes a longitudinal hole therethrough defining a containment balloon inflation lumen, the interior chamber of said containment balloon being in fluid communication with said containment balloon inflation lumen, and further including means for introducing a contrast medium into said containment balloon inflation lumen to fill the interior chamber of said containment balloon for verifying integrity of said containment balloon.

12. The apparatus of claim 11 further including means for perfusion of blood past said containment balloon when the interior chamber of said containment balloon is filled.

13. An apparatus for localized intravascular radiotherapy of a blood vessel, such as a coronary artery, comprising:

a catheter, said catheter comprising an elongate member having a proximal and a distal end, said elongate member being sized and of sufficient flexibility for introduction into a patient's body through a cardiovascular lumen until the distal end is disposed at a target area within the blood vessel, said elongate member further including a longitudinal hole therethrough defining a treatment balloon inflation lumen;

a treatment balloon, said treatment balloon comprising an inflatable balloon having an interior chamber, said treatment balloon being sealed to the distal end of said elongate member with the interior chamber of said treatment balloon in fluid communication with said treatment balloon inflation lumen;

means for introducing a fluid containing a radioactive material into said treatment balloon inflation lumen to fill the interior chamber of said treatment balloon for exposure of said target area to said radioactive material for a predetermined period of time; and an inert expansion balloon, said inert expansion balloon comprising an expandable balloon having an interior chamber, said inert expansion balloon being sealed to the distal end of said elongate member and contained within the interior chamber of said treatment balloon.

14. The apparatus of claim 13 wherein said elongate member further includes a longitudinal hole therethrough defining an inert expension balloon inflation lumen, the interior chamber of said inert expansion balloon being in fluid communication with said inert expansion balloon inflation lumen, and further including means for introducing a liquid into said inert expansion balloon inflation lumen to fill the interior chamber of said inert expansion balloon for reducing the volume of fluid containing a radioactive material used to fill the interior chamber of said treatment balloon.

15. An apparatus for localized intravascular radiotherapy of a blood vessel, such as a coronary artery, comprising;

a catheter, said catheter comprising an elongate member having a proximal and a distal end, said elongate member being sized and of sufficient flexibility for introduction into a patient's body through a cardiovascular lumen until the distal end is disposed at a target area within the blood vessel, said elongate member further including a longitudinal hole therethrough defining a treatment balloon inflation lumen;

a treatment balloon, said treatment balloon comprising an inflatable balloon having an interior chamber, said treatment balloon being sealed to the distal end of said elongate member with the interior chamber of said treatment balloon in fluid communication with said treatment balloon inflation lumen;

means for introducing a fluid containing a radioactive material into said treatment balloon inflation lumen to fill the interior chamber of said treatment balloon for exposure of said target area to said radioactive material for a predetermined period of time;

first and second blocking balloons, each balloon having an interior chamber, said first blocking balloon being sealed to the distal end of said elongate member distal of said treatment balloon, said second blocking balloon being sealed to the distal end of said elongate member proximal of said treatment balloon, said elongate member further including a blocking balloon inflation lumen, said blocking balloon inflation lumen comprising a longitudinal hole through said elongate member, the interior chambers of said first and second blocking balloons being in fluid communication with said blocking balloon inflation lumen; and means for introducing a liquid into said blocking balloon inflation lumen to fill the interior chambers of said first and second blocking balloons.

16. An apparatus for localized intravascular radiotherapy of a blood vessel, such as a coronary artery, comprising:

a catheter, said catheter comprising an elongate member having a proximal and a distal end and an outer surface, said elongate member being sized and of sufficient flexibility for introduction into a patient's body through a cardiovascular lumen until the distal end is disposed at a target area within the blood vessel, said elongate member further including a longitudinal hole therethrough defining a treatment balloon inflation lumen;

a sleeve-shaped treatment balloon, said sleeve-shaped balloon comprising an expandable, substantially cylindrical hollow sleeve having a substantially cylindrical inner wall and a substantially cylindrical outer wall defining a chamber therebetween, the inner wall of said sleeve-shaped balloon being attached to the outer surface of the distal end of said elongate member along a longitudinal line of contact with the chamber in fluid communication with said treatment balloon inflation lumen, at least a portion of said inner wall overlapping said outer wall in an unexpanded condition of said balloon;

means for expanding said sleeve against an interior wall of said blood vessel; and means for introducing a fluid containing a radioactive material into said inflation lumen to fill the chamber of said sleeve for substantially uniform exposure of said target area to said radioactive material for a predetermined period of time.

17. A method of preventing stenosis and restenosis of a selected portion of a blood vessel in a patient comprising:

selecting a catheter comprising an elongate member having a proximal and a distal end, and including a treatment balloon, said treatment balloon comprising an inflatable balloon attached to the distal end of said catheter, said catheter being sized and of sufficient flexibility for introduction into the selected portion of the blood vessel;

advancing the catheter along a cardiovascular lumen or the patient until said treatment balloon is disposed in the selected portion of the blood vessel adjacent a wall of said blood vessel;

inflating said treatment balloon with a liquid containing radioactive material;

maintaining said treatment balloon inflated with said liquid, the radioactive material in said liquid being substantially uniformly dispersed in said treatment balloon such that the wall of the blood vessel is substantially uniformly exposed to radiation from said radioactive material for a predetermined period of time;

withdrawing the liquid from said treatment balloon to allow said treatment balloon to collapse; and withdrawing said catheter from the patient.

18. The method of claim 17 further including relieving a stenosed region of the selected portion of the blood vessel by inflating said treatment balloon with said liquid to force said balloon against the walls of said selected portion to expand said stenosed region radially outward.

19. A method of preventing stenosis and restenosis of a selected portion of a blood vessel in a patient comprising:

selecting a catheter comprising an elongate member having a proximal and a distal end, and including a treatment balloon, said treatment balloon comprising an inflatable balloon attached to the distal end of said catheter, said catheter further including a containment balloon disposed about said treatment balloon, said catheter being sized and of sufficient flexibility for introduction into the selected portion of the blood vessel;

advancing the catheter along a cardiovascular lumen of the patient until said treatment and containment balloons are disposed in the selected portion of the blood vessel;

inflating said containment balloon with a radio-opaque contrast medium to verify integrity of said containment balloon prior to inflating said treatment balloon;

inflating said treatment balloon with a liquid containing radioactive material;

maintaining said treatment balloon inflated with said liquid for a predetermined period of time;

withdrawing the liquid from said treatment balloon to allow said treatment balloon to collapse; and withdrawing said catheter from the patient.

20. The method of claim 19 further including relieving a stenosed region of the selected portion of the blood vessel by inflating said containment balloon with liquid to expand said containment balloon against the walls of said selected portion to expand said stenosed region radially outward.

21. An apparatus for localized radiotherapy of a body lumen, such as a coronary artery, comprising:

an elongate member having a proximal and a distal end, said elongate member being sized and of sufficient flexibility to be introducible into a patient's body through a body lumen until the distal end is disposed at a target area within the body lumen, said elongate member further including a longitudinal passage therethrough;

a fluid expansible means connected to said elongate member in fluid communication with said passage for containing a fluid having a radioactive material therein; and means for introducing said fluid into said passage to expand said fluid expansible means toward an interior wall of said body lumen, the radioactive material in said fluid being substantially uniformly dispersed in said fluid expansible means such that the wall of the lumen is substantially uniformly exposed to radiation for a predetermined period of time.

22. The apparatus of claim 21, wherein said fluid expansible means contains a radioactive liquid.

23. An apparatus for localized intravascular radiotherapy of a blood vessel, such as a coronary artery, comprising:

a catheter, said catheter comprising an elongate member having a proximal and a distal end, said elongate member being sized and of sufficient flexibility for introduction into a patient's body through a cardiovascular lumen until the distal end is disposed at a target area within the blood vessel, said target area comprising a wall of the blood vessel, said elongate member further including a longitudinal hole therethrough defining a fluid passage;

an inflatable balloon connected to said elongate member and having an interior chamber in fluid communication with said fluid passage;

injector means connected to said elongate member for introducing a fluid through said fluid passage and into the interior chamber of the balloon under pressure; and a fluid in said interior chamber under pressure from said injector means so as to expand said balloon toward the wall of the blood vessel, a radioactive material substantially uniformly dispersed in said fluid such that the wall of the blood vessel is substantially uniformly exposed to radiation from said radioactive material for a given treatment time.

24. A method of localized radiotherapy of a selected portion of a body lumen in a patient comprising:

providing an elongate member having a proximal and a distal end, and a fluid expansible means attached to the distal end of said elongate member, said elongate member being sized and of sufficient flexibility for introduction into the selected portion of the body lumen;

advancing the elongate member along the body lumen of the patient until said fluid expansible means is disposed in the selected portion of the body lumen adjacent a wall thereof;

expanding the fluid expansible means with a fluid containing a radioactive material such that the radioactive material is substantially uniformly dispersed in the fluid expansible means;

maintaining said fluid in a non-ionizing environment in said fluid expansible means for a predetermined treatment time;

withdrawing said fluid from said fluid expansible means to allow said fluid expansible means to contract; and withdrawing said elongate member from the patient.

* * * * *